(12) United States Patent
Kutsch et al.

(10) Patent No.: US 7,458,464 B1
(45) Date of Patent: Dec. 2, 2008

(54) DENTAL APPLIANCE CARE KIT

(76) Inventors: V. Kim Kutsch, 1155 Twin Hills Dr., Jefferson, OR (US) 79352; Robert J. Bowers, 3170 26th Ave., SE., Albany, OR (US) 97322; Jesse L. Droesch, 3093 27th Ave., SE., Albany, OR (US) 97322; Steven R. Folin, 3479 Siuslaw Ct., NE., Albany, OR (US) 97321

( * ) Notice: Subject to any disclaimer, the term of this patent is extended or adjusted under 35 U.S.C. 154(b) by 60 days.

(21) Appl. No.: 11/709,102

(22) Filed: Feb. 20, 2007

Related U.S. Application Data

(60) Provisional application No. 60/775,373, filed on Feb. 21, 2006.

(51) Int. Cl.
*B65D 85/00* (2006.01)

(52) U.S. Cl. .................. 206/570; 206/63.5; 206/581

(58) Field of Classification Search ........... 206/570, 206/571, 572, 581, 368, 369, 63.5, 823
See application file for complete search history.

(56) References Cited

U.S. PATENT DOCUMENTS

| | | | |
|---|---|---|---|
| 4,115,293 A | | 9/1978 | Schoenholz et al. |
| 5,348,153 A | * | 9/1994 | Cole .................. 206/361 |
| 6,309,622 B1 | | 10/2001 | Watkins |
| 6,715,603 B1 | | 4/2004 | Uribe |
| 2004/0091839 A1 | * | 5/2004 | Fischer ............... 433/226 |
| 2004/0200748 A1 | * | 10/2004 | Klassen et al. ........ 206/368 |
| 2006/0042992 A1 | * | 3/2006 | Vulcano ............... 206/581 |
| 2007/0114139 A1 | * | 5/2007 | Moore .................. 206/63.5 |

OTHER PUBLICATIONS

SonicBrite Retainer Cleaning Kit two pages from web site www.dentakit.com.
Orthodontic Headgear and Dental Appliance Bag one page from web site www.dentakit.com.
Removable Appliance Care Kit one page from web site www.dentalmart.com.

* cited by examiner

*Primary Examiner*—Jacob K Ackun, Jr.
(74) *Attorney, Agent, or Firm*—Lori M. Friedman

(57) ABSTRACT

This invention comprises a kit of materials necessary for a patient to clean and maintain a dental appliance made of plastic resin. More specifically, the kit contains a special brush, a polishing paste, a gel for use under the appliance when worn, an oral care rinse to use with the appliance, a powdered material that is dissolved in water that becomes a solution that cleans and disinfects the appliance, and a plurality of protective cases.

11 Claims, 1 Drawing Sheet

DENTAL APPLIANCE CARE KIT

RELATED PATENT APPLICATIONS

Figure 1:
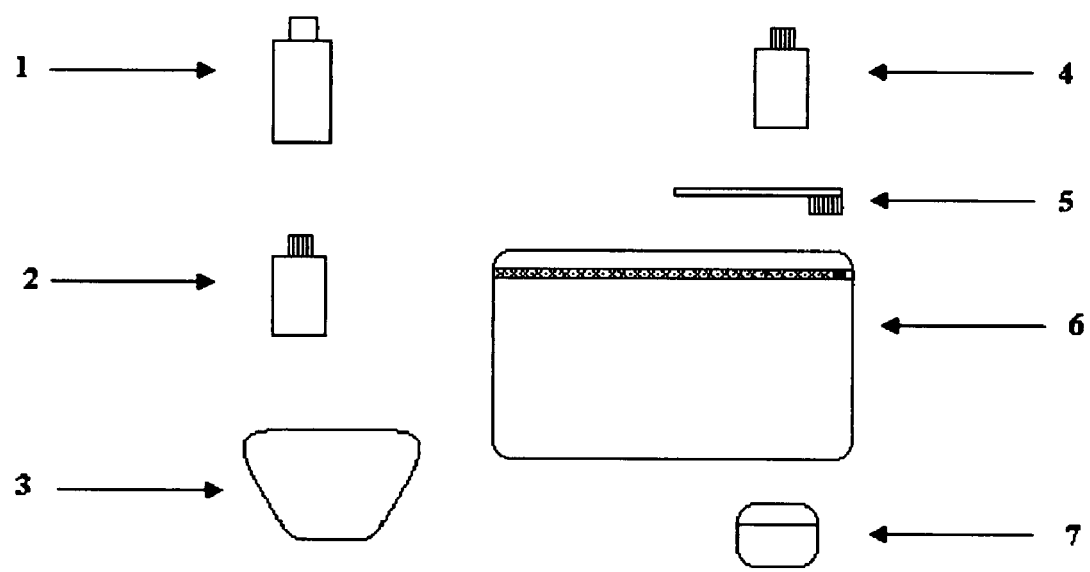

This is a utility patent application that claims the benefit of provisional application number 60/775,373 filed on Feb. 21, 2006 which is hereby incorporated by reference.

FIELD OF THE INVENTION

This invention comprises a kit of materials necessary for a patient to clean and maintain a dental appliance made of plastic resin. More specifically, the kit contains a special brush, a polishing paste, a gel for use under the appliance, when worn, an oral care rinse to use with the appliance, an effervescent cleaner used for cleaning and disinfecting the appliance, a plastic case to safely transport and protect the appliance; and a carrying case to safely transport and protect the appliance and each of the components of the kit.

BACKGROUND OF THE INVENTION

Being able to maintain and care for removable plastic dental appliances is an ever important issue, especially when the appliance is intended for cosmetic purposes. If not for the specially formulated materials of the present invention, the patients would use toothbrush and toothpaste meant for natural dentition, they will damage the appliance and make it rough and dull instead of smooth and shiny.

Maintaining removal dental esthetic appliances other than partial dentures has not been widely addressed. The market for cosmetic and other removable dental appliances made of synthetic resin is a growing field, and thus the need for the present invention.

In the past, there have been a number of dental care kits available. For example, a a web site to dental maet.com there is a "Removable Appliance Care Kit" which contains packets of denture cleanser, a denture brush, a sonic denture bath, a book of instructions and a carrying tote. At web site dentakit.com, an "Orthodontic Headgear and Dental Appliance Bag" is a nylon pouch that can carry orthodontic headgear, facebows, and other large removable dental appliances.

At dentakit.com, a "SonicBrite Retainer Cleaning Kit" is shown. The product includes a heavy-duty portable sonic cleaning bath with a built-in timer, a bottle of professional-strength cleaning powder, a measuring spoon, and instructions. In U.S. Pat. No. 6,715,603 Uribe discloses a Dental Care Kit. The invention is a small device, with size analogous to a credit card that contains a supply of dental floss and a dental cleaning implement. The components of Uribe's kit can be either one-use or multi-use. Denture cleansers are by no means new; the following two US patents feature denture cleansers that are analogous to the effervescent powder that is part of the instant kit.

The prior art, as described above is not comparable to the instant invention. Applicants' invention is a kit whose components deal with both keeping a patient's natural teeth healthy as well as keeping a removable acetal appliance in good appearance and condition.

SUMMARY OF THE INVENTION

The instant invention consists of a kit that includes a gel for the patient to wear inside of the appliance to protect the teeth from decay, a polishing gel to use specifically designed for plastic resin to keep it shiny and to use instead of toothpaste, a brush that has a larger handle like a denture brush but with small soft bristles specifically designed to clean synthetic resin, a type of mouth rinse that contains fluoride but is colorless so that it doesn't stain the appliance, an effervescent cleaner used for cleaning and disinfecting the appliance and a case for the appliance and a small zipper cosmetic carrying case for the kit.

FIGURES

FIG. 1 depicts the contents of the removable resin dental appliance care kit of the present invention

DETAILED DESCRIPTION OF PREFERRED EMBODIMENTS

The present invention involves the cleaning and maintenance of a removable dental appliance made of plastic. The types of appliances of this invention are selected from the group consisting of multiple unit temporary bridges, unilateral partial dentures, a removable occlusal overlay, provisional appliances, orthodontic removable appliances, orthodontic retainers, snore guard appliances, occlusal splints, night-guards, dental diet appliances, and cosmetic appliances. Of particular interest is an acetal appliance that is a cosmetic dental appliance that is a thin, flexible, resin shell of perfect teeth that snaps over the patient's natural dentition.

The dental appliances that are maintained by the materials and methods of this invention are selected from the group consisting of acetal resin, acrylic resin, nylon, polycarbonate, styrene resin, vinyl resin and other thermoplastic resins that are used in fabricating removable dental appliances With reference to FIG. 1 the components of the plastic removable appliance care kit are shown. With reference to 1, the oral rinse of this invention contains fluoride, xylitol, water, sodium benzoate, calcium hydroxide or sodium bicarbonate, natural flavors, ethanol, Poloxamer 407. The oral rinse is colorless so that it does not stain the appliance.

The components of the oral rinse are fluoride, as an anti-cavity protectant, sodium benzoate, sodium bicarbonate or calcium hydroxide present as pH adjusters. The pH of the mouth should be kept at a higher than neutral pH to maintain good oral health, to minimize cavities and maintain a healthy biofilm in the mouth. Xylitol is a sugar substitute. In addition to discouraging tooth decay by replacing dietary sugars, xylitol may actively aid in repairing minor cavities caused by dental caries. Recent research confirms a plaque-reducing effect and suggests that the compound, having some chemical properties similar to sucrose, attracts and then "starves" harmful micro-organisms, allowing the mouth to remineralize damaged teeth with less interruption.

Another ingredient in the oral rinse 1 of this invention is Poloxamer 407. Derived from natural gas and oil, Poloxamer 407 belongs to a category of ingredients generally known as surfactants. Surfactants have a special function: they make it possible for oil-based ingredients to be dissolved into a water-based solution. A surfactant molecule is characterized by its two distinct functional properties: a polar, hydrophilic property and a nonpolar, hydrophobic property. This dual receptivity allows oils to be dissolved into solution with water.

It is necessary to have such an ingredient in the oral rinse of this invention because the natural oils used for flavoring it would not otherwise mix with water and other ingredients of the oral rinse 1. Because Poloxamer 407 is a nonionic surfactant it is far less likely to react with the other ingredients that make up the formula of the oral rinse 1.

With further reference to FIG. 1, the resin appliance polishing gel 2 that cleans, maintains and protects the appliance comprises alcohol, sodium laurel sulfate as a cleanser, hydroxyethyl cellulose as a gelling agent, and silica as a polishing agent. The polishing gel 2 is brushed onto the appliance daily to clean, protect, and maintain the appliance;

The polishing gel 2 is brushed on the appliance with the specially provided brush 5. The brush 5 comprises small (from about 3 mil to about 9 mil in length) soft bristles that are made of nylon that clean, protect, and maintain the appliance.

The gel 4 that is worn inside the appliance comprises water, xylitol, a pH adjuster, sodium benzoate as a preservative, natural flavor, at least one natural oil, and Poloxamer 407 as a surfactant. All dental appliances increase the risk for dental caries on the remaining teeth of a patient, so this gel worn inside of the appliance when it is placed into the mouth reduces the bacterial biofilm, and protects the teeth from decay by increasing the pH, adding fluoride and antimicrobial agents to the surface of the teeth while the appliance is being worn.

Another component of the dental appliance care kit of this invention is an effervescent cleanser 7. The effervescent cleanser of this invention comprises citric acid as a reducing agent, sodium bicarbonate as an oxidizing agent, xylitol, potassium mono persulfate/potassium peroxomonosulfate complex available as the compound Oxone® as a bleaching agent, sodium benzoate as an anti-bacerial agent, and sodium lauryl sulfate as cleaning agent. Also present are xylitol as a bactericide and teaberry also known as wintergreen extract as a flavoring agent. Many dental appliances are hygroscopic and absorb the flavor of the water in which the appliance is immersed. In this way, the person will experience a pleasant flavor when orally inserting the appliance.

The kit of this invention also includes a plastic case 3 to safely transport and protect the appliance; and a carrying case 6 to safely transport and protect the appliance and each of the components of the kit.

Besides the kit and its components described, this invention also covers a method of maintaining dental health and the appearance and a removable dental appliance. The steps taken by a patient include rinsing with the oral rinse provided while wearing the appliance, applying the gel 4 to the inside of the appliance to provides decay prevention to the patient's teeth before putting the appliance in place, providing and daily using the polishing gel 2 specifically designed to clean, protect, and maintain the appliance.

When not in the mouth, the appliance should be protected by putting it into the plastic case 3 to safely transport and protect it. Furthermore, the appliance should be transported and protected by a carrying case 6 provided. The components of the kit can be placed in the carrying case 6.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A plastic dental appliance care kit for the regular cleaning and maintenance of a patient's natural teeth and simultaneously maintaining the appearance of a removable acetal dental appliance comprising
   a) a mouth rinse for a patient's use while wearing the appliance;
   b) a gel for the patient to wear inside of the appliance that provides decay protection and prevention to the patient's teeth;
   c) a polishing gel specifically designed to clean, protect, and maintain the appliance;
   d) a brush to be used with said gel that is likewise designed to clean, protect, and maintain the appliance;
   e) a powdered material, which when mixed with water dissolves and becomes an effervescent solution to clean and disinfect the dental appliance;
   f) a plastic case to safely transport and protect the appliance; and
   g) a carrying case to safely transport and protect the appliance and each of the components of the kit.

2. The kit of claim 1 wherein the appliance is selected from the group consisting of multiple unit temporary bridges, unilateral partial dentures, a removable occlusal overlay, provisional appliances, orthodontic removable appliances, orthodontic retainers, snore guard appliances, occlusal splints, night-guards, dental diet appliances, removable implant appliances and cosmetic appliances.

3. The kit of claim 2 wherein the appliance is a cosmetic dental appliance that is a thin, flexible, resin shell of perfect teeth that snaps over the patient's natural dentition.

4. The kit of claim 1 wherein the oral rinse contains fluoride, xylitol, water, sodium benzoate, a ph adjuster natural flavors, ethanol, Poloxamer 407 and is colorless so that it does not stain the appliance.

5. The kit of claim 1 wherein the gel worn inside the appliance comprises water, a thickening agent, xylitol, fluoride, a pH adjuster, sodium benzoate as a preservative and antimicrobial agent, natural flavors, at least one natural oil, and Poloxamer 407 as a surfactant.

6. The kit of claim 5 wherein the thickener is selected from the group consisting of hydroxyethyl cellulose, Carbopol®, and silica, the pH adjuster is selected from the group consisting of, calcium hydroxide, sodium bicarbonate and sodium hydroxide, the natural oil is glycerin.

7. The kit of claim 4 wherein the ph adjuster is sodium bicarbonate, the thickener is hydroxyethyl cellulose, and the natural oil is glycerin.

8. The kit of claim 1 wherein the polishing gel that cleans, maintains and protects the appliance comprises alcohol, sodium laurel sulfate as a cleanser, hydroxyethyl cellulose as a gelling agent, and silica as a polishing agent.

9. The kit of claim 1 wherein the brush to be used with said gel comprises small, from about 3 mil to about 9 mil in length soft bristles that are made of nylon that clean, protect, and maintain the appliance.

10. The kit of claim 1 wherein the plastic removable dental appliance is made of materials are selected from the group consisting of acetal resin, acrylic resin, nylon, polycarbonate, styrene resin, vinyl resin and other thermoplastic resins used in fabricating removable dental appliances.

11. The kit of claim 1 wherein the powdered cleanser and disinfectant comprises citric acid as a reducing agent, sodium bicarbonate as an oxidizing agent, xylitol as a bactericide, potassium mono persulfate/potassium peroxomonosulfate complex as a bleaching agent, sodium benzoate as an antibacterial agent, and sodium lauryl sulfate as cleaning agent, and wintergreen extract as a flavoring agent, said powdered cleanser when dissolved in water becomes an effervescent material, which when mixed with water dissolves and becomes effervescent to clean and disinfect the dental appliance.

* * * * *